United States Patent
Montgomery et al.

(10) Patent No.: US 6,778,857 B1
(45) Date of Patent: *Aug. 17, 2004

(54) ALPHA PARTICLE SUPPRESSION OF ELECTRONIC PACKAGING

(75) Inventors: David B. Montgomery, Scottsdale, AZ (US); James B. Hamilton, Canyon Country, CA (US); Ken R. Ulmer, Phoeniz, AZ (US)

(73) Assignee: Pacesetter, Inc., Sylmar, CA (US)

( * ) Notice: Subject to any disclaimer, the term of this patent is extended or adjusted under 35 U.S.C. 154(b) by 230 days.

This patent is subject to a terminal disclaimer.

(21) Appl. No.: 10/094,170

(22) Filed: Mar. 7, 2002

(51) Int. Cl.$^7$ .............................................. A61N 1/375
(52) U.S. Cl. ....................................................... 607/36
(58) Field of Search ........................... 607/36, 1, 2, 33, 607/37, 38

(56) References Cited

U.S. PATENT DOCUMENTS

| | | | | |
|---|---|---|---|---|
| 3,866,616 A | * | 2/1975 | Purdy et al. ................... | 607/36 |
| 4,326,095 A | | 4/1982 | Yamaguchi ................... | 174/52 |
| 4,764,480 A | * | 8/1988 | Vora ............................ | 438/203 |
| 5,019,409 A | | 5/1991 | Wesling et al. ................ | 427/96 |
| 5,334,245 A | | 8/1994 | Hartnett et al. ................ | 118/59 |
| 6,239,479 B1 | | 5/2001 | Hwang et al. ................. | 257/659 |
| 6,532,389 B1 | * | 3/2003 | Shahandeh .................... | 607/27 |

OTHER PUBLICATIONS

Emerson & Cuming Technical Data Sheet—Ablebond 7900 Encapsulant, 4/98, 2 sheets.
Metech Polymers Corp.—New Glob Top Materials G8342–1, G8340D, May, 23, 2000, 1 sheet.
Asymtek, Specifications: DV6000 Series Pump, Undated 2 sheets.
Asymtek, Specifications: DP3000 Series Pump, Undated, 2 sheets.
Asymtek, Process Platform: Centruy C–720 Series—Precision Batch Dispensing, 2 sheets.
Namics Corporation, Certificate of Compliance—Chipcoat G8342–1, Feb. 17, 2000, 1 sheet.

* cited by examiner

Primary Examiner—Jeffrey R. Jastrzab

(57) ABSTRACT

An implantable medical device in the form of a cardiac stimulation device such as a pacemaker or defibrillator includes a hermetically sealed housing having an inner peripheral surface, an electronic component such as an integrated electrical circuit sensitive to bombardment by alpha particles and located within the housing spaced from the inner peripheral surface, and blocking material intermediate the inner peripheral surface of the housing and the electronic component capable of suppressing alpha particles having an energy level up to about 15 mev directed towards the electronic component. The blocking material has a thickness of at least 0.010 inches; it may be sheet material; it may be congruently attached to the inner peripheral surface of the housing; or it may be a liquid coating applied to the inner peripheral surface and subsequently cured.

12 Claims, 2 Drawing Sheets

ALPHA PARTICLE SUPPRESSION OF ELECTRONIC PACKAGING

FIELD OF THE INVENTION

The present invention relates to an implantable medical device, such as a pacemaker or ICD (implantable cardioverter defibrillator) which employ electronic components including integrated electronic circuitry within a hermetically sealed housing. More particularly, to the present invention relates to a system for suppressing alpha particles, which may be directed towards the electronic components.

BACKGROUND OF THE INVENTION

Implantable stimulation devices of the type having electronic circuit components are well known in the medical arts. In one particularly common form, the implantable device comprises a pacemaker unit having an appropriate electrical power supply and related control circuitry for use in electrically stimulating a patient muscle, such as the heart. Such pacemaker units commonly include an hermetically sealed case or housing within which the power supply and control circuitry are protectively encased, in combination with one or more conductive pacemaker leads extending from the housing to the selected muscle structure within the patient. Feed-through terminals on the pacemaker housing accommodate hermetically sealed passage of electrical conductors to the housing exterior for appropriate connection to an implantable lead.

These implantable devices such as pacemakers and cardiac defibrillators employ the implantable electrical leads for passing electrical signals between the device and the heart. To insure an uninterrupted electrical path between the device and the heart, a strong reliable mating between the implantable leads and the connector top of the device is necessary. It is also desirable to seal the entrance of the connector top of the device from body fluids.

Substantial advances have been gained over the years in overcoming problems of sealing and connecting the components, for example. However, another persistent problem addressed by the present invention concerns the presence of alpha particles in the environment which can disrupt the electronic circuitry, specifically, data in Static Random Access Memory (SRAM) integrated circuits which are at the core of an implantable medical device. Alpha particles are naturally occurring and can be emitted by numerous materials that are used in the construction of pacemaker and ICD devices. Pacemakers and ICDs routinely use SRAM circuitry so it is imperative that the SRAM devices be protected from alpha particles.

Alpha particles can disrupt data in Static Random Access Memory (SRAM) integrated circuits. Alpha particles have low energy and can be stopped by a thin layer of material that does not itself emit alpha particles. The semiconductor industry has developed many commercially available materials used to coat semiconductors used in multi-chip modules (MCM). One family of materials is typically used to "glob top" integrated circuits. These materials are deposited onto the integrated circuits and then cured to a hard coating. The inherent drawbacks of using glob top materials is that rework and failure analysis are severely curtailed by the hard coating.

Such efforts made previously to shield electronic circuitry against external influences are found in the patent literature. Typical instances of a known techniques are disclosed in U.S. Pat. No. 5,019,409 to Wesling et al. and U.S. Pat. No. 5,334,245 to Hartnett et al., each of which concerns a method of, and apparatus for, dispensing a thin coating of a highly viscous encapsulant liquid on the top surface of a semiconductor device. U.S. Pat. No. 6,239,479 to Hwang et al. discloses a thermal neutron shield for integrated circuits which deters absorption of thermal neutrons by circuit constituents to form unstable isotopes with subsequent decay which generates bursts of charge which may upset stored charge and create soft errors.

It is noteworthy that none of the prior art is concerned with implantable medical devices but is in light of the foregoing that the present invention was conceived and has now been reduced to practice.

SUMMARY OF THE INVENTION

The present invention relates to an implantable medical device in the form of a cardiac stimulation device such as a pacemaker or defibrillator which includes a hermetically sealed housing having an inner peripheral surface, an electronic component such as an integrated electronic circuit sensitive to bombardment by alpha particles and located within the housing spaced from the inner peripheral surface. Blocking material is provided intermediate the inner peripheral surface of the housing and the electronic component capable of suppressing alpha particles having an energy level up to about 15 mev directed towards the electronic component. The blocking material has a thickness of at least 0.010 inches; it may be sheet material; it may be congruently attached to the inner peripheral surface of the housing; or it may be a liquid coating applied to the inner peripheral surface and subsequently cured.

Experiments have shown that as little as 0.010 of an inch of certain glob top materials will stop 100% of alpha particles up to 15 mev of energy. By coating the inside surface of the housing of the MCM, for example, the alpha particles can be stopped without coating the integrated circuit directly. This technique protects the SRAM from upset and yet allows for easy rework and failure analysis.

Other and further features, advantages, and benefits of the invention will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention, and together with the description, serve to explain the principles of the invention in general terms. Like numerals refer to like parts throughout the disclosure.

BRIEF DESCRIPTION OF THE DRAWINGS

The foregoing aspects and other features of the present invention are explained in the following description, taken in connection with the accompanying drawings, wherein.

DETAILED DESCRIPTION OF THE PREFERRED EMBODIMENT

Figure 1:
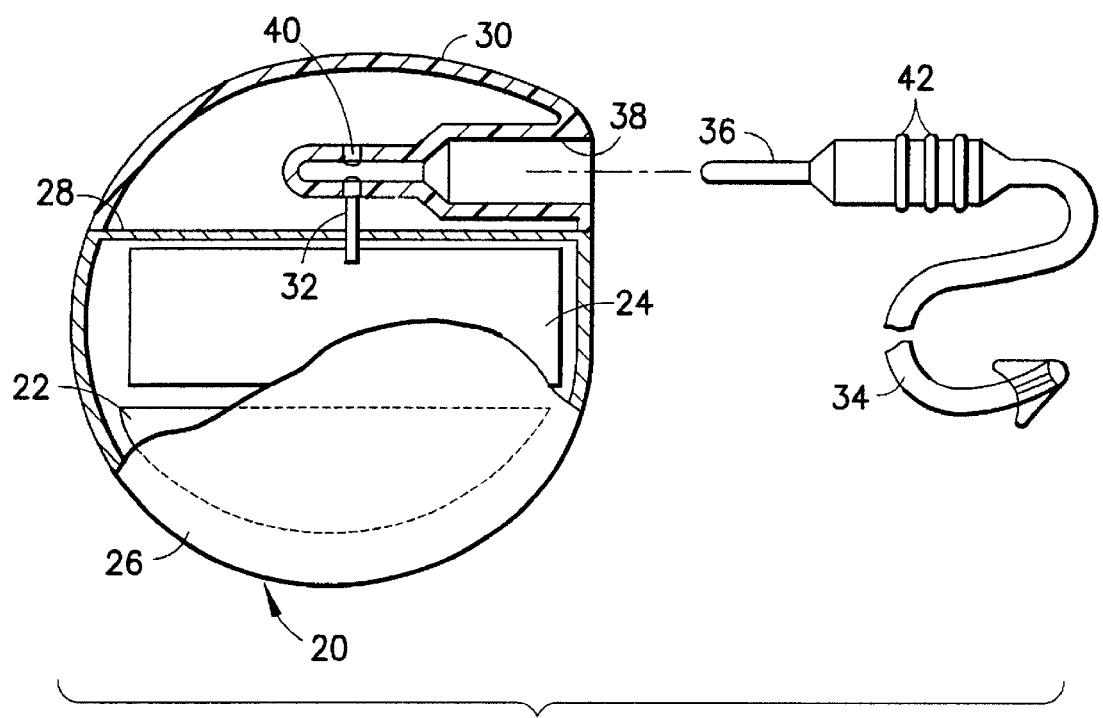
FIG. 1 is a diagrammatic side elevation view, largely in section, conceptionally illustrating the layout and hermetically sealed area of a pacemaker embodying the present invention.

Although the present invention will be described with reference to the embodiments shown in the drawings, it should be understood that the present invention can be embodied in many alternate forms or embodiments. In addition, any suitable size, shape or type of elements or materials could be used. In order to appreciate the advantages of the present invention, it will help first to have a basic understanding of the manner in which the mechanical and electrical connection functions are carried out in prior art pacemakers, for example. Referring now to the drawings and, initially, to FIG. 1, a pacemaker 20 is shown, which includes a battery 22 that powers integrated electronic circuitry 24. The electronic circuitry 24 and battery 22 are mechanically housed and in a suitable housing 26 (preferably hermetically sealed). Typically, this housing or case is shaped to include a flat side or platform 28 to which a suitable epoxy connector 30 can be bonded. At least one feedthrough terminal 32, in electrical contact with the integrated electronic circuitry 24, passes through the case or housing 26 and protrudes out from the platform 28. This feedthrough terminal 32 is electrically isolated from the case 26.

A pacemaker lead 34, having a proximal terminal 36, connects to the pacemaker integrated electronic circuitry 24 by inserting the proximal terminal 36 into a receiving channel 38 of the connector 30 until the proximal terminal is in contact with a conductive portion 40 electrically isolated from the case 26 but electrically coupled to the circuitry 24 via the feed through terminal 32. Sealing ribs or ridges 42 on the connecting end of the pacemaker lead are designed to tightly engage the inside edges of the receiving channel 38 in order to prevent any body fluids from entering into the receiving channel once the connecting end of the lead 34 has been inserted into the connector 30.

Figure 2:
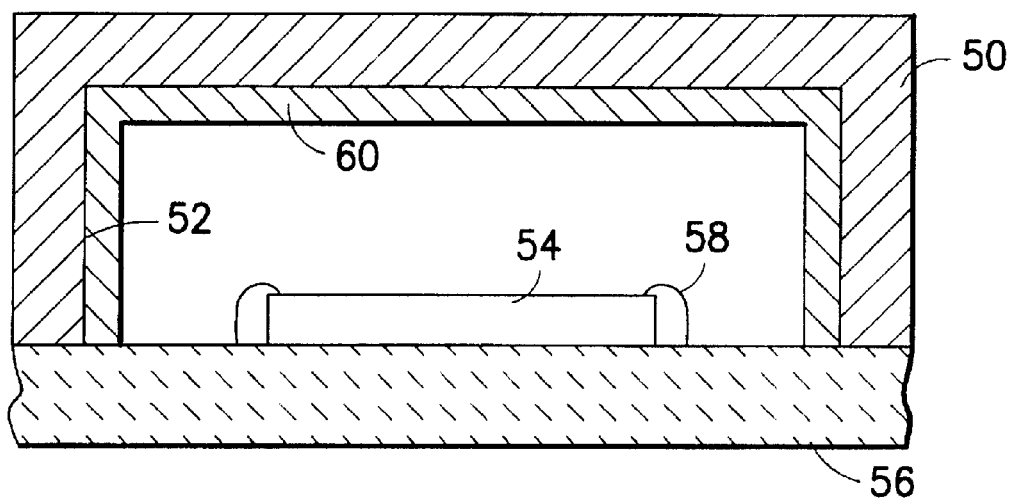
FIG. 2 is a diagrammatic section view illustrating one embodiment of the invention.

For a discussion of the invention which is applicable to the integrated electronic circuitry 24 of FIG. 1, turn now to FIG. 2. It should be appreciated that the implantable medical device intended to employ the invention may be a pacemaker, or ICD, a combination pacemaker/defibrillator, or any other Implantable medical device of the type having electronic circuit components. As seen in FIG. 2, a portion of such a device is diagrammatically illustrated as including a hermetically sealed housing 50 having an inner peripheral surface 52. An electronic component 54 is located within the housing 50 spaced from the inner peripheral surface 52 and, in a customary fashion, is sensitive to bombardment by alpha particles. The electronic component 54 may be integrated electronic circuitry but the invention need not be so limited. As illustrated, but not intended to be limiting of the invention, the electronic component 54 is mounted on a substrate 56 of suitable material with wire bonds 58 typically connecting, electrically, the electronic component 54 to underlying circuitry within the substrate.

Blocking material 60 is positioned intermediate the inner peripheral surface 52 of the housing 50 and the electronic component 54 and is of a composition capable of suppressing alpha particles directed towards the electronic component, preferably capable of suppressing alpha particles having an energy level up to about 15 mev. One suitable composition for purposes of the invention is known as Ablebond® 7900 low expansion chip encapsulant, also referred to as an ionically clean glob top encapsulant, available from Emerson & Cumming with offices in Billerica, Mass., USA. Another suitable glob top material composition for purposes of the invention is known as Chipcoat G8342-1 and G8340D for encapsulating ICs, available from Metech Polymers Corporation with offices in Carson City, Nev., USA.

In one embodiment, blocking material 60 may be congruently attached to the inner peripheral surface 52 of the housing, for example, being a liquid coating applied to the inner peripheral surface and subsequently cured. In this configuration, or any other, it is important that the blocking material have a thickness of at least 0.010 inches. This is necessary in order for the blocking material to be properly effective. More specifically, the thickness is based on the material properties of the encapsulant or blocking material and the energy spectra of the alpha particle source.

Figure 3:
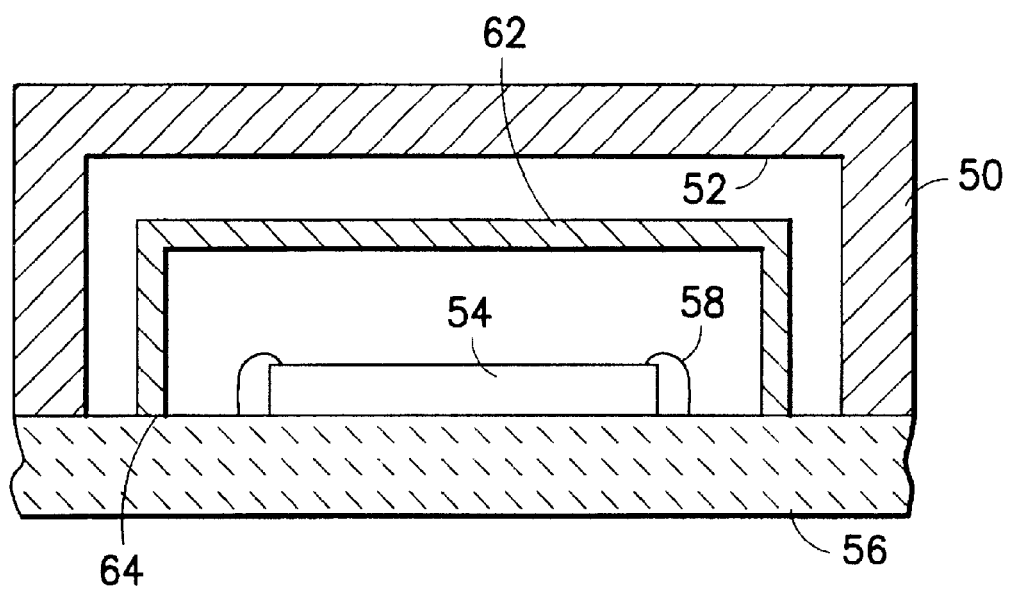
FIG. 3 is a diagrammatic section view, similar to FIG. 2 illustrating another embodiment of the invention.

In another embodiment, as shown in FIG. 3, blocking material 60 includes sheet material 62 which is suitably bonded around its periphery 64 to the underlying ceramic substrate 56, for example, and completely overlies the electronic component 54, but at all times remains spaced from the electronic component.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

What is claimed is:

1. An implantable medical device comprising:
   a sealed housing having an inner peripheral surface;
   an integrated electrical circuit located within the housing and spaced from the inner peripheral surface; and
   a layer of blocking material interposed between the inner peripheral surface of the housing and the integrated electrical circuit, wherein the material is capable of suppressing alpha particles directed towards the integrated electrical circuit.

2. An implantable medical device as set forth in claim 1:
   wherein the layer of blocking material is capable of suppressing alpha particles having an energy level up to about 15 mev.

3. An implantable medical device as set forth in claim 1 including:
   wherein the layer of blocking material has a thickness of at least about 0.010 inches.

4. An implantable medical device as set forth in claim 1:
   wherein the blocking material comprises sheet material.

5. An implantable medical device as set forth in claim 1:
   wherein the blocking material is congruently attached to the inner peripheral surface of the housing.

6. An implantable medical device as set forth in claim 1:
   wherein the blocking material comprises a liquid coating applied to the inner peripheral surface and subsequently cured.

7. An implantable medical device as set forth in claim 1:
   wherein the implantable medical device comprises a cardiac stimulation device.

8. An implantable medical device as set forth in claim 7:
   wherein the cardiac stimulation device comprises a pacemaker.

9. An implantable medical device as set forth in claim 7:
   wherein the cardiac stimulation device comprises a defibrillator.

10. An implantable medical device as set forth in claim 7:
    wherein the cardiac stimulation device comprises a combination pacemaker/defibrillator.

11. An implantable medical device as set forth in claim 1:
    wherein the integrated electrical circuit is a static random access memory integrated circuit.

12. An implantable medical device as set forth in claim 1:
    wherein the integrated electrical circuit is a random access memory integrated circuit.

* * * * *